(12) United States Patent
Efstathiou et al.

(10) Patent No.: US 6,843,991 B1
(45) Date of Patent: Jan. 18, 2005

(54) USE OF THE M3 PROTEIN OF MHV68 TO BLOCK BINDING OF A CHEMOKINE TO ITS RECEPTOR

(75) Inventors: Stacey Efstathiou, Cambridge (GB); Antonio Alcami, Cambridge (GB); Christopher Marc Parry, Cambridge (GB); Vincent Peter Smith, Cambridge (GB); João Pedro Monteiro e Louro Machado de Simas, Lisboa (PT)

(73) Assignee: Cambridge University Technical Services Limited, Cambridge (GB)

( * ) Notice: Subject to any disclaimer, the term of this patent is extended or adjusted under 35 U.S.C. 154(b) by 0 days.

(21) Appl. No.: 09/617,178

(22) Filed: Jul. 17, 2000

(30) Foreign Application Priority Data

Jul. 16, 1999 (GB) .............................................. 9916703

(51) Int. Cl.$^7$ .............................................. A61K 39/12
(52) U.S. Cl. .................... 424/186.1; 530/826; 530/350; 435/375; 435/7.2; 435/7.3; 436/501; 424/193.1; 424/229.1
(58) Field of Search ........................... 424/186.1, 193.1, 424/229.1, 85.1, 85.2, 192.1, 195.1, 195.11, 196.11, 198.1, 204.1, 225.1; 435/375, 7.2, 7.3, 7.1, 5, 7.8; 530/826, 350, 351; 436/501

(56) References Cited

U.S. PATENT DOCUMENTS 5,428,130 A    6/1995  Capon et al.

FOREIGN PATENT DOCUMENTS

| WO | WO 95 12673 | 5/1995 |
| WO | WO 97 44054 | 11/1997 |
| WO | WO 98 36766 | 8/1998 |
| WO | WO 01/21204 | 3/2001 |

OTHER PUBLICATIONS van Berkel et al. J. Virol. 2000; 74:6741–6747.*
Parry et al. (Journal of Experimental Medicine (2000) 191(3): 573–578).*
U.S. provisional application No. 60/154,799, McFadden et al., filed Sep. 20, 1999.
Van Berkel, Victor et al., "Identification and initial characterization of the murine gammaherpesvirus 68 gene M3, encoding an abundantly secreted protein", *Journal of Virology*, vol. 73, No. 5, May 1999, pp. 4524–4529.
Lalani, A.S. et al., "Modulating chemokines: more lessons from viruses", *Immunology Today*, GB, Elseveier Publications, Cambridge, vol. 21, No. 2, Feb. 2000, pp. 100–106.
Guerico et al., "Binding of a peptide antigen of multiple HLA alleles allows definition of an A2–like supertype", *Journal of Immunology*, 1995, 154, pp. 685–693.
Alcami and Smith, "Vaccinia, cowpox, and camelpox viruses encode soluble gamma interferon receptors with novel broad species specificity", *Journal of Virology*, Aug. 1995, pp. 4633–4639.
Engeman et al., "Inhibition of functional T Cell priming and contact hypersensitivity responses by treatment with anti-secondary lymphoid chemokine antibody during Hapten sensitization", *Journal of Immunology*, [2000] 164, pp. 5207–4214.
Tsung et al., "Gene expression and cytopathetic effect on vaccinia virus inactivated by psoralen and long–wave UV light", *Journal of Virology*, [1996] 70, pp. 165–171.
Fauci, "Host factors and the pathogenesis of HIV–induced disease", *Nature*, vol. 384, Dec. 12, 1995, pp. 529–534.
Horuk et al., "A receptor for the malarial parasite *Plasmodium vivax*: The erythrocyte chemokine receptor", *Science*, vol. 1261, Aug. 24, 1993, pp. 1182–1184.
Parry et al., "A broad spectrum secreted chemokine binding protein encoded by herpesvirus", *Journal of Experimental Medicine*, Feb. 7, 2000, vol. 191, No. 3, pp. 573–578.
Alcami and Smith, "A soluble receptor for interluekin–1β encoded by vaccinia virus: a novel mechanism of virus modulation of the host response to infection", *Cell*, 1992, 71, pp. 153–167.
Upton et al., "Encoding of a homolog of the IFN–gamma receptor by myxoma virus", *Science*, 1992, 258, pp. 1369–1372.
Chastel et al., A herpesvirus from an Europian Schrew (*Crodidura Russula*), *Acta Virologica*, 1994, 38, p. 309.

* cited by examiner

Primary Examiner—Lorraine Spector
Assistant Examiner—Zachary C. Howard
(74) Attorney, Agent, or Firm—Klarqust Sparkman, LLP (57) ABSTRACT

A pharmaceutical composition comprises M3 protein as encoded by virus MHV 68, or a homologue of said M3 protein, for use in binding to a chemokine or a chemokine analogue in vivo, or to block binding of chemokines to corresponding cell surface receptors in vivo, to produce an immunomodulatory effect, or to bind to a chemokine analogue present in a virus or parasite to block its entry into cells.

22 Claims, 6 Drawing Sheets

M3 inhibits binding of MIP-1α to their natural receptors expressed on U937 cells.

M3 inhibits binding of IL-8 to their natural receptors expressed on U937 cells.

FIG. 5

Heparin and heparin sulfate do not interfere with the capacity for M3 to bind to radio-labeled IL-8 or MIP-1α.

FIG. 6

M3 inhibits RANTES induced Ca$^{2+}$ flux in human PBMCs in a dose dependent manner.

FIG. 7a

M3 inhibits MCP-1 induced migration of THP-1 cells in a dose dependent manner.

FIG. 7b

M3 inhibits IL-8 induced migration of neutrophils in a dose dependent manner.

FIG. 8

Effect of M3 on contact sensitivity inflammatory response in mice.
Values represent mean difference in ear-thickness between control and challenged ears ± SD. Statistical analysis was performed between M3 treated groups (10 and 100μg/injection) and the ovalbumin (Pva) control group (100μg/injection) using Student's T-test (*$p<0.05$).

USE OF THE M3 PROTEIN OF MHV68 TO BLOCK BINDING OF A CHEMOKINE TO ITS RECEPTOR

FIELD OF THE INVENTION

This invention relates to the use of viral proteins and analogues thereof as binding partners for immune system components and analogues thereof, and to related compositions and methods, for example pharmaceutical compositions and methods, and detection or assay reagents and kits and methods.

BACKGROUND OF THE INVENTION

Among known herpesvirus proteins is a protein encoded by gene M3 of murine gammaherpesvirus 68 (MHV68) (V van Berkel et al: J Virol 73(5) (1999) pp 4524–4529).

Protein M3 of MHV68 has been reported to be a secreted protein. It has been suggested that this protein may modulate the host immune response to infection by the virus.

The present invention arises from a new finding of particular binding properties of M3 protein of MHV68.

BRIEF DESCRIPTION OF THE DRAWINGS

FIG. 7 is a set of two graphs (7(a) and 7(b)). Graph 7(a) shows that M3 inhibits MCP-1 induced migration of THP-1 cells, and graph 7 (b) shows that M3 inhibits IL-8 induced migration of neutrophils.

SUMMARY AND DESCRIPTION OF THE INVENTION

According to an aspect of the present invention, M3 protein and its functional homologues, including derivatives, and fragments, can be used to bind chemokines of the immune system and their analogues, and to block binding of chemokines to corresponding cell surface receptors. M3 can for example act as a useful immunosuppressant. Details of these binding effects of M3 protein are described herein below.

Homologues of M3 protein can be obtained, e.g. by mutation of an M3-encoding nucelotide sequence and expression from the mutated sequence, and/or by use or derivation from related gene sequences, e.g. from herpesvirus from Crocidura russula (Bowden, 1997, Cambridge University PhD thesis and Chastel et al, Acta Virologica 1994 38:309).

Alternatively, they can be obtained, e.g. by identifying gene sequences homologous to M3 by screening databases containing either protein sequences or nucleotide sequences encoding proteins, for example by screening the Swissprot database in which homology can be determined using the Blast program, e.g. using any of the possible algorithms, for example set to default parameters. An acceptable level of homology over the whole sequence is at least about 20%, e.g. about 30%. Homology of a functional fragment of M3 with other proteins can be lower than this, e.g. about 10%.

Functional homologues, including derivatives or fragments, of M3 can be checked for their capacity to bind any or all of the chemokines mentioned below by appropriate equivalents of the cross-linking assays described herein, using for example radiolabelled chemokine. Other related proteins, e.g. of MHV 68, for example the M1 protein of MHV 68 can also have useful chemokine binding properties. This can also be assessed for example by cross-linking assays described herein, or appropriate equivalents readily derivable therefrom.

The protein can for example be used to bind either chemokines and their analogues with an animal species origin or specificity corresponding to the host range of the parent virus from which the protein comes, and/or chemokines and their analogues with human origin and/or specificity.

M3 protein can for example be used to bind C chemokines, CC chemokines, CXC chemokines or CX3C chemokines, for example the following: human lymphotactin (C chemokine); RANTES, MIP-1-alpha, MCP-1, MCPA (CC chemokines); IL-8, murine KC, murine MIP2, murine LIX, human GCP2, human IP10 (CXC chemokines); and fractalkine (CX3C chemokine).

In accordance with an aspect of the invention, M3 protein and its homologues, including derivatives or fragments, can be used to inhibit the binding of such chemokines to their receptors, whether in-vitro, e.g. in biological samples, or in-vivo.

This effect can be exploited for example in specific binding tests using labelled reactants, e.g. for diagnostic and measurement purposes. The labelled reactant can be either the M3 protein, or the chemokine, or the chemokine receptor, according to the configuration of the test for desired purposes in hand.

The test configuration, and the corresponding form and composition of the reagents, can be selected from among known specific binding test configurations: e.g. ELISA tests; analogues of the original hormone radioimmunoassay configuration of Yalow and Berson, etc. Generally the test configuration involves contacting a biological sample with a labelled and/or immobilised form of a material with chemokine valency and/or a chemokine-binding agent, wherein the material with chemokine valency will normally be selected from chemokines as listed herein above, and compounds that can interfere with the binding of such a chemokine to its receptor, in order to detect or assay a substance with chemokine valency or its receptor possibly present in the sample.

Accordingly, an aspect of the invention also lies in compositions for carrying out such tests, e.g. the labelling product of M3 protein or a homologue, e.g. a derivative or a fragment; calibrated test aliquots of either of these; the product of binding M3 protein or a homologue to a solid phase suitable to take part in a specific binding test as mentioned herein; calibrated test aliquots of one of the binding partners in the reaction; and test kits associating two or more of such reagents.

The test can be for example an assay for a chemokine or for a chemokine receptor. Examples of such tests can be arranged using variants of the binding test methods described in detail below.

The binding effect can also be exploited in the inhibition of effects mediated by chemokines that can be bound by the M3 protein or its homologues.

For example, it is known that in psoriasis IL8 is a mediator of pathological effects in skin. The binding effect described here can be used either in diagnostic methods to assess the degree of dependence of skin effects upon IL8 in a given case, or to produce a useful degree of inhibition of such effects.

In such a diagnostic method, sample material from skin tissue under test can be subjected to specific binding assay as indicated above to assess the presence and/or level of chemokine such as IL-8.

In an inhibitory treatment method, protein M3 or an analogue thereof, e.g. a derivative or fragment, can be applied to skin tissue either locally or systemically to modulate the interaction between chemokine and its receptor in the tissue.

According to a further aspect of the invention a pharmaceutical composition can comprise M3 protein, or a homologue thereof, e.g. a derivative or fragment, as mentioned above, for use as an anti-inflammatory agent, in appropriate therapeutic (anti-inflammatory) amount.

According to a further aspect of the invention, a gene encoding M3 or a homologue thereof, e.g. a derivative or fragment, can be inserted under control of a suitable promoter, e.g. a strong tissue-specific or constitutive promoter such as the HCMV IE promoter, in a gene delivery system, e.g. for use in gene delivery in vivo. The gene delivery system can be a viral or non-viral vector system. Such a vector can be used to confer on a target transfected cell the ability to produce M3 protein or a homologue thereof, e.g. a derivative or fragment, e.g. for anti-inflammatory purposes when the target cell is in-vivo in a host that is the subject of treatment. Such anti-inflammatory purposes can include for example use to inhibit effects mediated by chemokines, e.g. by chemokines which promote or are associated with disease, for example an inflammatory disease such as psoriasis or rheumatoid arthritis. Anti-inflammatory purposes also include reduction of host immune response against elements of the vector delivery system and/or against other gene products expressed in the target cell after gene delivery by a vector system, whether it is from the same vector as that which delivers the M3 gene or from a separate delivery vector for such another delivered gene.

Amongst derivatives of M3 which are within the scope of the invention are polypeptides having M3 sequences modified by deletion or substitution, which retain the chemokine-binding property of M3. For example, it can be useful to delete any immunogenic amino acid motifs, for example any which are found to bind to MHC molecules, or replace such motifs with a less immunogenic amino acid sequence. Examples of immunogenic motifs are described in M–F Guercio et al., 1995, J. Immunol., 154, pp 685–693. Alternatively, a modification which can induce immunological tolerance in a host can be introduced into the M3 sequence.

M3 protein, e.g. purified recombinant M3 protein, can be formulated with compatible per se conventional pharmaceutical excipients for delivery to a subject to be treated.

M3 protein or vectors expressing M3 can be administered to cells in vivo, for example by any suitable systemic delivery route. Alternatively the administration can be targeted, e.g. by direct injection, such as by intravenous injection at or near the site of the target cells and/or site of inflammation in the subject to be treated. Amounts of M3 protein which can usefully be administered range from about at least 1 microgram per kg (weight of subject to be treated). When treatment is carried out by use of a vector that can express M3, e.g. a herpesvirus, it can be useful to deliver such a vector in a dose in the range of about $1 \times 10^3$ to about $10^{13}$ pfu of virus, e.g. in the range of about $1 \times 10^3$ to about $1 \times 10^8$ pfu of virus.

The M3 or homologue thereof can also be administered in other ways, e.g. intravenously in a deaggregated protein form, for example as a single subunit. Forms of administration can be chosen to limit the immune response of the host to M3. For example, the M3 protein or vector expressing M3 can be delivered with another immunosuppressant (other than the M3 itself) or anti-inflammatory substance, for example with a corticosteroid, methotrexate or with a derivative of the OX40 receptor, e.g. a fusion protein comprising a sequence from OX40 fused to a constant domain of an IgG molecule, e.g. as described in WO 95/12673 (Stanford University and Becton Dickinson: W Godfrey et al).

Immunogenicity of native and/or modified M3 protein can be assessed by injection of the M3 protein into an animal, e.g. a mouse, followed by measurement of the resulting immune response, e.g. by measuring both the antibody and T cell mediated responses using standard known methods.

In further examples of the invention, M3 protein and homologues thereof, including derivatives or fragments, can be coupled with other substances, either covalently or non-covalently. A suitable coupling partner is for example polyethylene glycol (PEG). Other coupling products can be fusion proteins, such as fusion proteins incorporating Ig constant-domain sequences. An M3 homologue can for example be produced as a fusion protein, wherein M3 or a truncated M3 sequence is fused at its C terminal to the N terminal of at least one constant domain of an IgG molecule, made by methods analogous to those described in U.S. Pat. No. 5,428,130 (Genentech). Such coupled products can have desirable pharmacokinetic properties, such as extended half-life in vivo. Fusion proteins can also show improve avidity of the 9M3 moiety for its binding target and can also, as in the case of lg fusions, provide an additional useful effector function.

For certain purposes, coupling partners be coupled to M3 or its homologue by known chemical coupling methods, for example biotinylation of one partner and derivatisation of the other with a binding partner of biotin, such as avidin.

In certain embodiments of the invention, a functionally active truncated M3 protein, i.e. an M3 protein homologue with a truncated sequence can be used, e.g. in vivo. Truncated proteins can possess increased ability to penetrate tissues, e.g. at sites of inflammation, in comparison to the native M3.

In further embodiments of the invention M3 protein and homologues thereof, including derivatives or fragments, can be usefully modified in further ways, for example, by fusion of M3 to other chemokine binding proteins (or with active fragments or derivatives thereof), e.g. to the chemokine-binding protein Serp 1. Such modified proteins can have an altered binding specificity for chemokines, for example, so that the modified form of M3 can bind with a higher or lower affinity to certain classes of chemokines relative to the unmodified form of M3.

Such modified M3 proteins with altered binding specificity relative to native M3 can be especially useful for treating certain inflammatory disorders or diseases characterised by activity of particular types of chemokines, e.g. IL8 is associated with psoriasis.

Binding activity of such coupled, truncated or modified M3 proteins can in general be checked using appropriate equivalents of the cross-linking assays described herein, using for example radiolabelled chemokine.

The invention extends to nucleotide sequences (e.g. DNA cassettes incorporating suitable promoters encoding M3 protein and its modified forms including homologues, such as fragments or their fusion products with other polypeptides, e.g. as described above), and such expression cassettes included in suitable plasmids or other vectors, e.g. viral vectors.

The invention, and materials and methods applicable to carrying out embodiments thereof, is further illustrated, but without intent to limit its scope, by the following description and accompanying drawings, which are described in further detail below, and of which:—

Referring to the drawings, and to the descriptions of materials and methods given below:—

The inventors have verified, as described herein, that MHV68 encodes a soluble chemokine binding protein with broad specificity. In the first place, such activity has been detected in MHV68-infected cell culture supernatants. Analysis of the MHV68 genome has indicated that a unique ORF, M3, could be predicted to encode a secreted protein of around 40 kDa. The M3 ORF has been deleted from the MHV68 genome to check if the M3 ORF encodes the chemokine binding activity. A revertant virus in which the M3 ORF was reinserted into the virus genome was also constructed to control for interactions elsewhere in the viral genome. The supernatants from wild type MHV68 and the M3 revertant infections formed a complex with [125I] RANTES after crosslinking, while the supernatants from the M3 deletion infection and the mock infection did not produce a complex (see FIG. 1).

Figure 1:
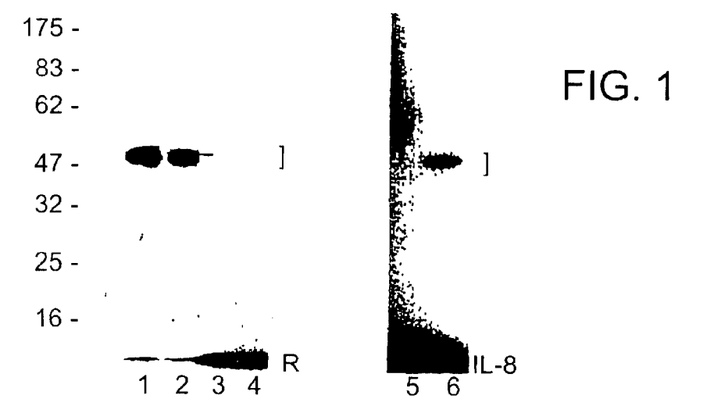
FIG. 1 is a set of auto-radiographs of SDS-PAGE analysis, with molecular masses in kDa, from experiments in which soluble chemokine binding activity is produced by MHV68.

FIG. 1 shows soluble chemokine binding activity produced by MHV68. For lanes 1–4, media from cultures uninfected (mock) or infected with MHV68 were incubated with [125I] RANTES and treated with the crosslinker BS3. The amount of medium used was equivalent to 5×10^2 cells. Lanes 5 and 6 media from mock baculovirus or baculovirus/M3 infected cells were incubated with [125I] IL-8 and treated with the crosslinker BS3. Auto-radiographs of the SDS-PAGE analysis, with molecular masses in kDa, are shown. The positions of RANTES (R), IL-8 and ligand-receptor complexes (square brackets) are indicated. Lane 1: MHV68 Wild Type, Lane 2: MHV68 M3 Revertant, Lane 3: MHV68 M3 Deletion, Lane 4: Mock, Lane 5: Baculovirus AcB 15R, Lane 6: BaculovirusIM3.

Binding assays with [125I] IL-8 (CXC chemokine), [125I] RANTES and [125I] MIP-1 (CC chemokines) and [125I] Fractalkine (CX3C chemokine) were carried out with MHV68 infected cell supernatants followed by chemical crosslinking with BS3. Complexes were detected with all three classes of chemokine tested; the mock infections did not produce any complexes (FIG. 1 and other data not shown in the Figures). The size of the complex in all cases was around 45 kDa, suggesting a MHV68 chemokine binding protein sized around 40 kDa after the size of the radiolabelled ligand was subtracted. Binding was detected whith a representative member of the CXC and CC and the single member of the CX3C subfamilies of chemokines indicating a broad binding specificity.

To further demonstrate that the protein encoded by M3 was capable of binding chemokines, a recombinant baculovirus was constructed which expressed the M3 ORF as protein. The supernatants from insect cells infected with this recombinant baculovirus/M3 was found to form a complex with [125I] IL-8 (FIG. 1) of a similar size to that observed with MHV68 infected cell supernatants. Therefore the inventors conclude that the chemokine binding activity of the MHV68 infected cell supernatants is attributable to the product of the M3 ORF.

Figure 2:
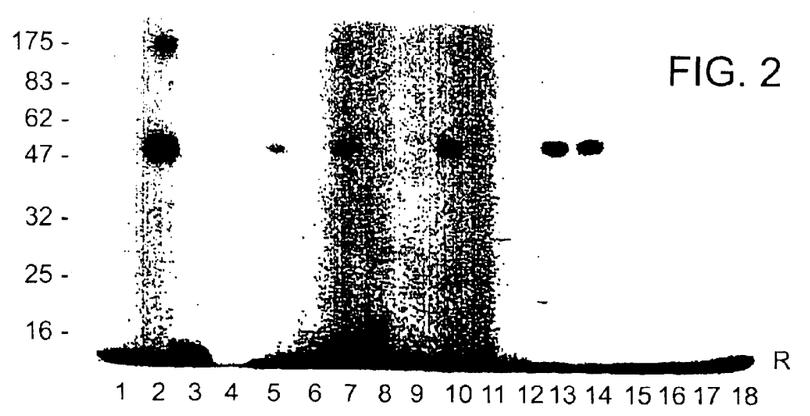
FIG. 2 is an auto-radiograph of another SDS-PAGE analysis from an experiment to show binding specificity of the soluble chemokine binding protein encoded by the MHV68 M3 ORF.

In order to determine the binding specificity of the product of the M3 ORF, crosslinking experiments were carried out with 2000 molar excess of unlabelled chemokine competitors. The binding to [125I] RANTES was competed to some extent by all the unlabelled chemokine competitors tested which included members from all four of the subfamilies (CXC, CC, C and CX3C) and examples of human and mouse chemokines (FIG. 2). The different intensities of the bands suggested different affinities of the M3 protein for different chemokines. Further experiments indicated that M3 binding to IL-8 and MIP-1 could also be competed with Exodus-2 (also known as secondary lymphoid tissue chemokine SLC) as well as those chemokines listed in FIG. 2.

FIG. 2 shows binding specificity of the soluble chemokine binding protein encoded by the MHV68 M3 ORF, by crosslinking of 0.4 nM human [125I] RANTES with BS3 to medium from uninfected (mock) and infected cultures, in the absence (Lane 2) or in the presence of 2000-fold excess unlabelled chemokines from different species (Lanes 3–18). The amount of medium was equivalent to 5×10^2 infected cells. An auto-radiograph of the SDS-PAGE analysis showing the ligand-receptor complexes is shown. Lane 1: Mock infected cells, Lane 2: MHV68 infected cells uncompeted, Lane 3: Human RANTES, Lane 4: Mouse RANTES, Lane 5: Human MIP-1, Lane 6: Mouse MIP-1, Lane 7: Viral MIP-2, Lane 8: MCP-1, Lane 9: MCP4, Lane 10: Murine KC, Lane 11: Human GRO, Lane 12: Human IL-8, Lane 13: Murine MIP-2, Lane 14: Murine LIX, Lane 15 Human GCP-2, Lane 16: IP-10, Lane 17: Human Lymphotactin, Lane 18: Fractalkine.

It has further been shown that the MHV68 soluble chemokine binding protein, M3, can block binding of chemokines to cell surface receptors.

Figure 3:
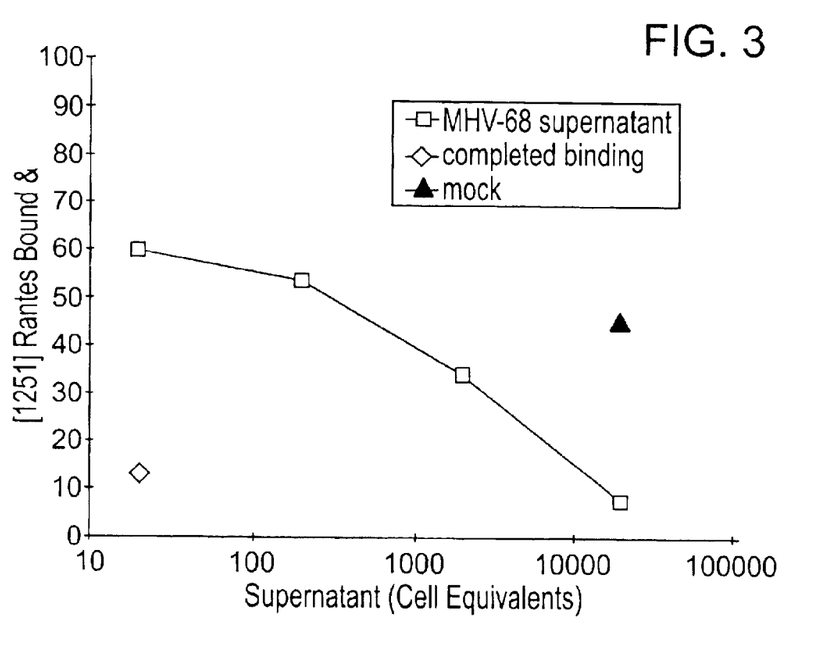
FIG. 3 is a graph showing binding of [$^{125}$I] RANTES to test (U937) cells in the presence of different amounts of MHV68-infected cell supernatants expressed as cell equivalents.

Thus, a biological activity of M3 for CC chemokines was shown by the ability of supernatants from MHV68 infected cells to inhibit the binding of [125I] RANTES to cellular receptors. The binding of [125I] RANTES to U937 cells was inhibited in a dose-dependent manner by MHV68 infected cell supernatants (FIG. 3). These results indicated that the soluble protein encoded by the M3 ORPF blocks the binding of CC chemokines to their high affinity cellular receptors. This was consistent with a high affinity interaction of RANTES and other CC chemokines with the M3 protein and strongly suggested that this viral chemokine binding protein is a potent inhibitor of the biological activity of chemokines, which is mediated by interaction with their cellular receptors.

FIG. 3 illustrates binding of [125I] RANTES to U937 cells in the presence of different amounts of MHV68 infected cell supernatants expressed as cell equivalents. A single point is shown for mock infected supernatants (20000 cell equivalents) and a single point representing 100-fold excess of unlabelled RANTES. Means from duplicate samples are expressed as a percentages of counts binding in the absence of a competitor.

Figure 4A:
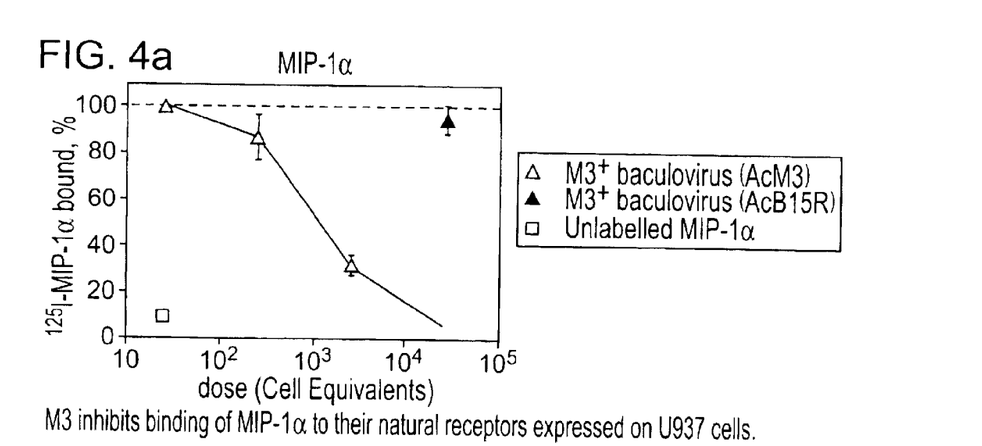
FIG. 4 is a set of two graphs (4 (a) and 4 (b)) showing binding of MIP-1 alpha and IL-8 to U937 cells respectively.
Figure 4B:
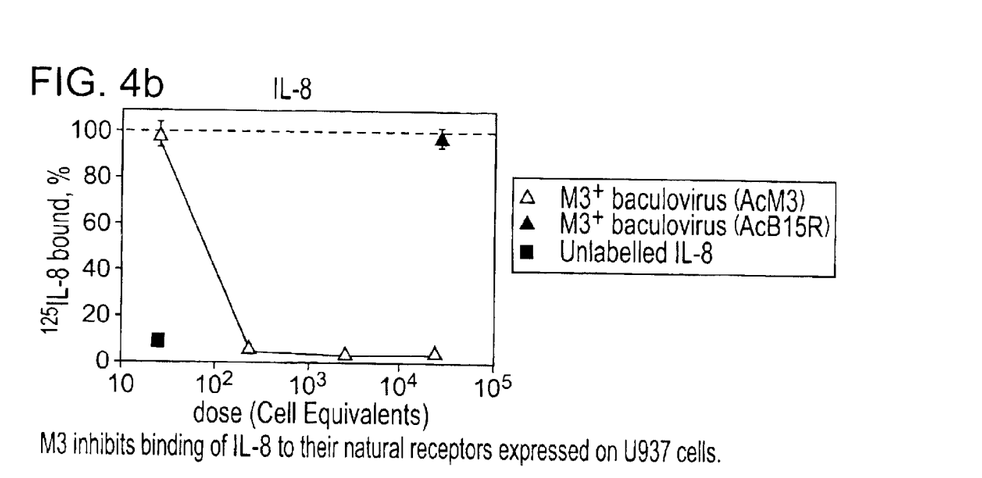

FIGS. 4a and 4b respectively illustrate binding of [1251] MIP-1 alpha and of [1251] IL-8 to U937 cells in the presence of different amounts of recombinant M3 produced in baculovirus. Supernatants from cells infected with baculovirus which does not express M3 and unlabelled MIP-1 alpha or IL-8 respectively are shown as controls as for FIG. 3. FIG. 4, parts (a) and (b), respectively show that M3 inhibits binding of MIP-1 alpha and IL-8 to their natural receptors expressed on U937 cells.

The fact that M3 blocks binding of chemokines to high-affinity chemokine receptors in U937 cells is regarded as an indication that the affinity of M3 for chemokines is similar to or better than that reported for the cellular chemokine receptors.

The inhibition of chemokine binding to cells as described herein can be achieved with very low doses of M3, which also gives an indication that it is a potent inhibitor of chemokine-receptor binding.

Inhibition of chemokine binding to cells by M3 appeared to be stronger for human IL-8 than for the other cytokines tested. This may indicate some degree of specificity of M3 binding to certain chemokines.

Figure 5:
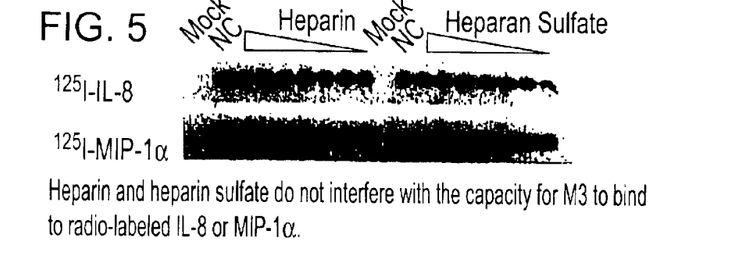
FIG. 5 is an auto-radiograph of SDS-PAGE analysis experiments involving binding of M3 to MIP-1 alpha and IL-8 respectively.

FIG. 5 illustrates that M3 does not bind to the GAG motif of proteins. Preincubation with heparin or heparin sulphate (which both contain a GAG motif) had no effect on binding of IL-8 or MIP-1 alpha to M3, i.e. heparin and heparin sulphate do not interefere with the capacity for M3 to bind to radio-labelled IL-8 or MIP-1 alpha.

Figure 6:
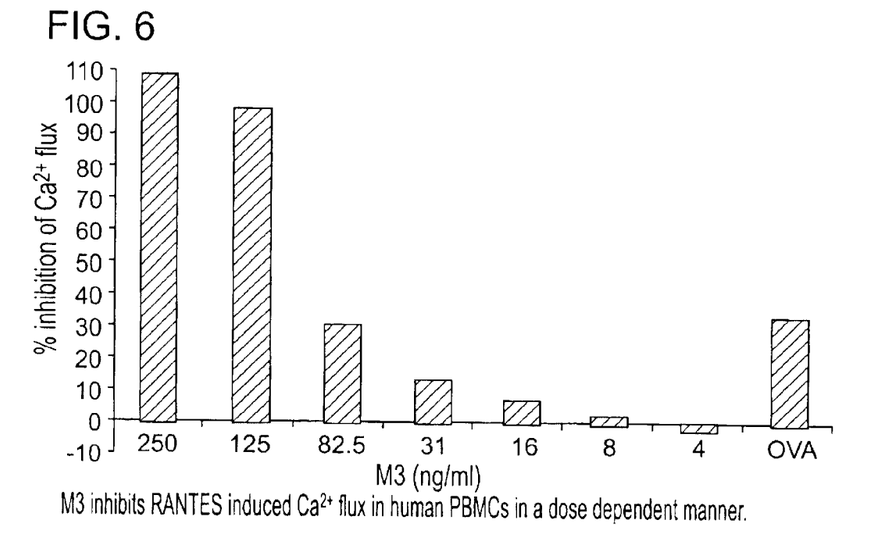
FIG. 6 is a graph showing results of inhibition experiments with M3, cultured cells and RANTES and demonstrates that M3 inhibits RANTES induced calcium flux in human PBMCs in a dose dependent manner.

FIG. 6 illustrates inhibition of calcium flux by varying amounts of purified M3 protein in peripheral blood mononuclear cells (PBMCs) stimulated with 50 ng/ml of RANTES. Control shown is PBMCs stimulated with RANTES and ovalbumin. The results show that M3 inhibits RANTES-induced calcium flux in human PBMCs in a dose dependent manner.

Figure 7A:
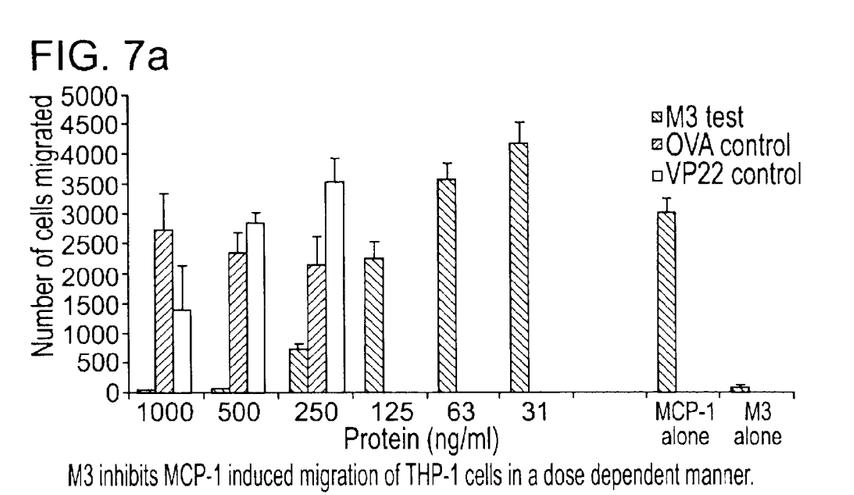
Figure 7B:
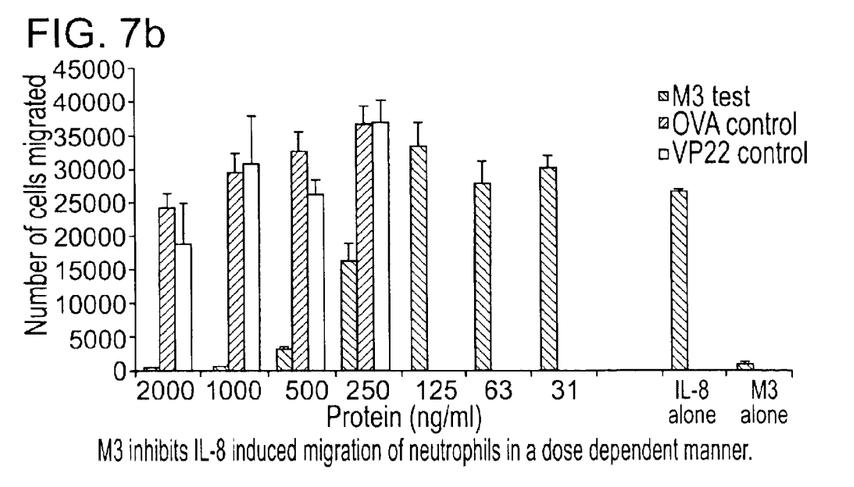

FIG. 7, parts (a) and (b) respectively illustrate inhibition, by varying amounts of purified M3 protein, of THP-1 cell migration in cells exposed to 50 ng/ml of MCP-1 (part (a)), and of neutrophil cell migration in cells exposed to 50 ng/ml of IL-8 (part (b)). Controls shown are: cells incubated with either chemokine or M3 alone and cells incubated with chemokine and also a control protein which is VP22 or ovalbumin. The results show that M3 inhibits MCP-1 induced migration of THP-1 cells and IL-8 migration of neutrophils in a dose dependent manner.

Figure 8:
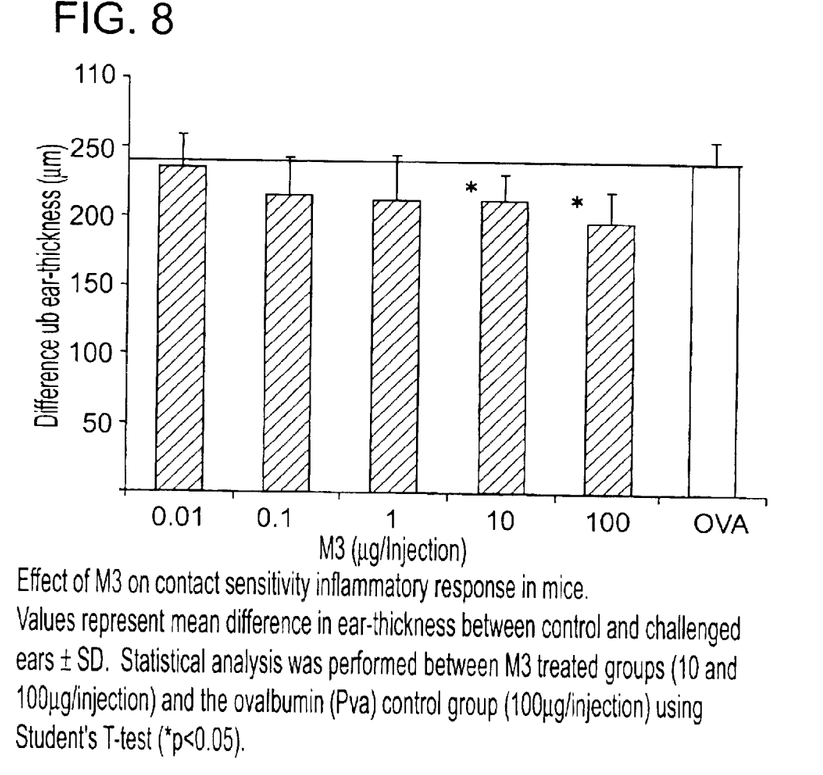
FIG. 8 is a graph showing results of in-vivo experiments for the effect of M3 on inflammatory responses in mice.

FIG. 8 illustrates the effect of purified M3 protein on the contact sensitivity inflammatory response in vivo in a mouse model. The magnitude of response is determined by measuring the difference in mouse ear thickness in sensitised animals by comparison with challenged and non-challenged ears of the same animal. M3 is shown to reduce ear inflammation in mice challenged with oxazolone. The values shown in FIG. 8 represent mean differences in ear-thickness between control and challenged ears plus or minus S.D.

Statistical analysis was performed between M3 treated groups (10 and 100 microgram/injection) and the ovalbumin (OVA) control group using students T-test (*$p<0.05$).

MATERIALS AND METHODS

Viruses and Infected Cell Supernatants

Viruses were grown and assayed on BHK 21 cells. Supernatants were prepared from BHK cells infected at 5 pfu per cell; the inoculum was removed after 2 hours and infected cells overlaid with Glasgow modified Eagles Medium (GMEM). Two days post infection the supernatants were collected, cellular debris removed by centrifugation and HEPES buffer (pH 7.5) was added to a final concentration of 20 mM. Supernatants were inactivated with 4,5',8-trimethylpsoralen and UV light (Tsung et al., 1996).

Reagents

Radioiodinated recombinant human IL-8, RANTES and MIP-1 (2000 Ci/mmol) were obtained from Amersham (Little Chalfont, UK). Recombinant human RANTES was obtained from R&D Systems (Minneapolis, Minn.). Recombinant human macrophage inflammatory protein-I (MIP-I), viral MIP-2 from human herpesvirus-8, monocyte chemoattractant protein (MCP)-1, MCP-4, human interleukin-8 (IL-8), GRO—, IFN-inducible protein 10 (IP-10), GCP2, lymphotactin, fractalkine and mouse RANTES, murine MIP-1, murine KC, murine MIP2, and murine lipopoysaccharide-induced CXC chemokine (LIX) were obtained from PeproTech (Rocky Hill, N.J.).

Binding Assays

Binding medium was RPMI 1640 containing 20 mM HEPES (pH 7.4) and 0.1% BSA. Crosslinking experiments with Bis(sulfosuccinimidyl) suberate (BS3) (50 M) to [1251]-chemokines (0.4 nM) were performed in 25 1 as described (Alcami & Smith, 1995, Upton et al., 1992). Samples were analysed by 12% acrylamide SDS-PAGE gels. In the competition assays with U937 cells, supernatants were pre-incubated with 100 pM [1251] chemokine in 100 1 for 1 h at 4 C. Subsequently, 2.5×10^6 U937 cells were added in 50 and incubated for 2 h at 4 C. Bound [1251] chemokine was determined by phthalate oil centrifugation as described (Alcami & Smith, 1992).

Construction of Recombinant Baculovirus

The MHV68 M3 ORF was amplified from infected cell DNA by PCR using oligonucleotides 5'-CGCGAATTCATGGCCTTCCATCCACATCG-3' (SEQ ID NO: 1) inserting an EcoRI site and 5'-GGTGCGGCCGCATGATCCCCAAAATACTCCAGC-3' (SEQ ID NO:2) which inserts a NotI site. The 1238 base pair product was digested with EcoRI and NotI and before being ligated in to EcoRI, NotI digested pBAC-1 (Novagen) creating pBACM3 The ORF was confirmed by sequencing before recombinant baculoviruses were produced as described (Alcami & Smith, 1995). Recombinant M3 protein containing a C-terminal 6 histidine tag was produced in sf21 insect cells infected with recombinant baculovirus. The recombinant baculovirus AcB 15R expressing the vaccinia virus soluble IL-1 receptor has been described (Alcami & Smith, 1992).

On occasion it has been found convenient to purify the recombinant M3 containing the histidine tag, by first concentrating the supernatant containing the protein by membrane filtration, and then dialysing the concentrate against phosphate buffered saline solution (PBS), and afterwards purifying the dialysis product on a Nickel-NTA column (Qiagen), in per se known manner.

Purified recombinant protein product has been used for example as follows:—

To Determine Whether M3 Binds to the Gag Binding Motif of Chemokines

Binding assays were carried out as described above except that radiolabelled IL-8 and MIP-1 alpha were pre-incubated with overloading amounts of heparin or heparin sulphate prior to addition of MHV-68 supernatents containing M3. Preparation of Peripheral blood mononuclear cells (PBMC's) for use in calcium flux assay PBMC's were isolated from whole blood using standard methods, such as those described in Current Protocols in Immunology, Vol. 2, Ed. By R. Coico, Wiley and Sons, U.S.A.

Isolated cells were then washed in Hanks buffered saline solution (HBSS, Gibco, UK) containing 1% foetal calf serum, followed by re-suspension (to a concentration of $1 \times 10^7$ cells/ml) in HBSS lacking calcium and magnesium salts (Gibco, UK). The cells were then mixed with the Fluo-4AM (4 micromolar final concentration, obtained from Molecular Probes) and pluronic F-127 labels (0.02% final concentration, obtained from Molecular Probes). This was followed by incubation of the cells (20 min, 37 deg C.). The labeled cells were then diluted (I in 5) in HBSS containing 1% foetal calf serum and incubated for 40 min at 37 deg C. Cells were washed and resuspended in HEPES buffered saline ($1.1 \times 10^6$ cells/ml) and incubated for 10 min, 37 deg C. 950 microliters of the cell suspension were then removed into a FACS tube and kept at 37 deg C for the calcium flux assay.

Calcium Flux Assay

RANTES protein (PeproTech) and purified M3 protein (produced in recombinant baculovirus as described above) were diluted before use in buffered saline. Thirty microliters of both RANTES (2 microgram/ml) and M3 (of varying concentration ranging from 10 micrograms/ml to 0.16 micrograms/ml) were mixed together and incubated for 6 minutes at room temperature. Fifty microliters of the mixture was then added to 950 microliters of PBMC's (obtained as described above). Controls were PBMC's stimulated with RANTES alone and also cells stimulated with a mixture of RANTES and ovalbumin (at a final concentration of 250 ng/ml). The calcium flux of the cells was measured by determining cell fluorescence using a FACS sort machine (Becton Dickinson) and the Cell Quest Program.

Percentage inhibition of calcium flux was determined as follows:

% inhibition=((fluorescence of RANTES control-fluorescence of RANTES and M3)/fluorescence of RANTES control)×100.

Growth Of THP-1 Cells And Neutrophils for use in Cell Migration Assay

THP-1 cells (obtained from the european culture collection (ECACC)) were grown (37 deg C in a humidifed atmosphere containing 5% carbon dioxide) in RPMI-1640 medium (Sigma) containing 10% heat inactivated foetal calf serum (Sigma), penicillin (100 International Units/ml) and streptomycin (100 mg/ml). Prior to the cell migration assay cells were washed in HBSS containing 1% human serum albumin and resuspended in tissue culture wells at a concentration of $1 \times 10^7$ cells per ml.

Neutrophils were isolated from whole human blood using standard methods, for example those described in Current Protocols in Immunology, Vol. 2, Ed. By R. Coico, Wiley and Sons, U.S.A.

Cell Migration Assay

Seventy five microliters of both MCP-1 (10 ng/ml in HBSS and containing 1% human serum albumin) and M3 (varying concentrations ranging from 1000 ng/ml to 31 ng/ml) were mixed and incubated for 15 minutes at 37 deg C. At the end of incubation 29 microliters of the mixture was added to the lower well of a transwell migration chamber (ChemoTX (TM), Receptor Technologies, Oxon, UK) and human monocytes ($2.5 \times 10^5$ per well) were added to the top well. A polycarbonate membrane (5 micron pore size) separated the two wells. The chamber was then incubated for 2 hours at 37 deg C in a humidified atmosphere containing 5% carbon dioxide. At the end of this incubation period cells that were within the membrane were removed and added to the lower well by incubation of the membrane with EDTA followed by centrifugation. Number of cells which had migrated was determined by counting the cells in the lower well using a haemocytometer. Controls were buffer alone in the lower well and also chemokine alone in the lower well.

Migration of neutrophils in presence of IL-8 and M3 was determined as described above for migration of THP-1 cells except for the following: IL-8 was used at a concentration of 200 ng/ml and was diluted in PPMI containing 0.5% foetal calf serum. Neutrophils were added to the top well of the chamber at a concentration of $5 \times 10^4$ cells per well. A membrane with a 3 micron pore size was used in the experiments and the chamber was incubated for 1 hour.

In Vivo Contact Sensitivity Assay

Contact sensitivity in the mouse is a well known animal model of inflammation. Mice (6 per group) were sensitised against oxazolone (Sigma) a known sensitising agent and treated over a period of time as follows On day 0, 25 microliters of oxazolone (3% solution in acetone (4 parts) and olive oil (I part) was painted onto the mouse abdomen and microliters onto each hind foot pad. On day 5, 10 microliters of 0.6% oxazolone was painted onto the right ears of mice and as a control 10 microliters of acetone/olive oil onto the left ears. On days -1, 0, 1, 4 and 5 mice were injected intraperitoneally with 100 microliters of purified M3 protein (containing from 0.1 micrograms to 100 micrograms of M3), ovalbumin was used as a control. On day 6, ear thickness was measured using engineers calipers. A measure of the inflammatory response was the difference in ear thickness between the right and left ears of the mice.

Further references cited in the methods section herein are as follows:—

Alcami, A. & Smith, G. L. (1992). A soluble receptor for interleukin-1 encoded by vaccinia virus: a novel mechanism of virus modulation of the host response to infection. Cell 71, 153–167.

Alcami, A. & Smith, G. L. (1995). Vaccinia, cowpox and camelpox viruses encode interferon- receptors with novel broad species specificity. J. Virol. 69, 4633–4639.

Engeman, T. M., Gorbachev, A. V., Glague, R. P, Heeger, P. S., & Fairchild, R. (2000). Inhibition of functional T cell priming and contact hypersensitivity responses by treatment with anti-secondary lymphoid chemokine antibody during hamster sensitisation. J. Immunol. 164, 5207–5214.

Tsung, K., Yim, J. H., Marti, W., Buller, R. M. L. & Norton, J. A. (1996). Gene expression and cytopathic effect of vaccinia virus inactivated by psoralen and long-wave UV light. J. Virol. 70, 165–171.

Upton, C., Mossman, K. & McFadden, G. (1992). Encoding of a homolog of the IFN-gamma receptor by myxoma virus. Science 258, 1369–1372.

The present invention also can be applied to the interaction of viruses such as human immunodeficiency virus and parasites such as *Plasmodium vivax* with attachment proteins on the surface of the target cells that they infect.

This application includes methods of inhibiting infection of susceptible cells by viruses such as human immunodeficiency virus and parasites such as *Plasmodium vivax*.

Since the M3 protein binds chemokines in solution and thus mimics the interaction of chemokines with cellular chemokine receptors, the M3 protein can also be expected to interact with the process of HIV or P. vivax infection.

In particular, it is expected that M3 protein can bind to attachment protein of HIV or Plasmodiurm vivax and thus prevent the binding of HIV or P. vivax to chemokine receptors in the host cell and/or subsequent entry into cells. M3 protein can thus be used to depress or prevent infection of target cells by these pathogens, and thus can protect or assist in protecting an individual from HIV or P. vivax infection. M3 protein can also be used to study the interaction of HIV and P. vivax with their target cells.

Chemokine receptors are known to play a critical role in transmission and dissemination of HIV by acting as a cofactor required together with CD4 for virus entry and infection (Fauci, 1996, Nature 384:529). The importance of chemokine receptor CCR5 in vivo is evidenced by the finding that individuals who are homozygous for a mutant version of the CCR5 gene are resistant to HIV infection. Binding of chemokines or mutated chemokine antagonists to chemokine receptors can block HIV infection, illustrating the potential of the blockade of HIV-chemokine receptor interaction as a preventive and therapeutic strategy against HIV.

The malaria parasite *Plasmodium vivax* is known to use a chemokine receptor of unknown function (Duffy antigen) to enter and infect erythrocytes (Horuk et al., 1993, Science 261:1182). Similarly to HIV infections, binding of chemokines to the Duffy antigen blocks infection of erythrocytes by P. vivax, and individuals that lack the Duffy antigen on their red cells are resistant to P. vivax malaria. Thus, blockade of the interaction of the malaria parasite with Duffy antigen by M3 and homologues can be expected to be of use in connection with P. vivax infection, whether for intervention, investigation, or for development of drugs for P. vivax.

An inhibitor of virus or parasite interaction with chemokine receptor can be used to prevent or depress infection following transmission, e.g. in cases of accidental injection with HIV contaminated material. The M3 protein can also be used in combination with other anti-HIV therapies (none of them 100% effective).

The natural ligands of M3 are chemokines. Since gp120 of HIV is known to mimic chemokines and interact with chemokine receptors, M3 can be expected to interact with HIV gp120, particularly as it has such a broad binding specificity for chemokines as is shown herein. However, the affinity of M3 for gp120 may not be as high as it is for chemokines which are the natural ligand of M3.

According to an aspect of the invention, therefore, in-vitro DNA mutagenesis on the basis of the M3 gene can be used to create modified forms of M3, from which mutants can be selected that bind better to the gp120 of HIV (or to the attachment protein in P. vivax). (With the exception of a poxvirus 35K chemokine binding protein, M3 is the only soluble protein known to bind chemokines. So M3 protein can be used as a good starting point to develop such binding agents/inhibitors.

Thus, the M3 protein can be used as a starting material for mutation work with a view to deriving soluble proteins that can bind with higher affinity than M3 itself to the domain of HIV gp120 which interacts with the cellular chemokine receptor, so as to facilitate blocking of HIV infection at an early stage. The M3 protein can also be used as a starting material for mutation work with a view to deriving agents to block attachment of P. vivax to the Duffy antigen on erythrocytes and initiation of infection.

The similarity between two nucleic acid sequences, or two amino acid sequences, may be expressed in terms of the similarity between the sequences, otherwise referred to as sequence identity. Sequence identity is frequently measured in terms of percentage identity; the higher the percentage, the more similar the two sequences are.

Methods of alignment of sequences for comparison are well known in the art. Various programs and alignment algorithms are described in: Smith & Waterman Adv. Appl. Math. 2: 482, 1981; Needleman & Wunsch J. Mol. Biol. 48: 443, 1970; Pearson & Lipman Proc. Natl. Acad. Sci. USA 85: 2444, 1988; Higgins & Sharp Gene, 73: 237–244, 1988; Higgins& Sharp CABIOS5: 151–153, 1989; Corpet et al. Nuc. Acids Res. 16, 10881–90, 1988; Huang et al. Computer Appis. in the Biosciences 8, 155–65, 1992; and Pearson et al. Meth. Mol. Bio. 24, 307–31, 1994. Altschul et al. (J. Mol. Biol. 215:403–410, 1990), presents a detailed consideration of sequence alignment methods and homology calculations.

The NCBI Basic Local Alignment Search Tool (BLAST) (Altschul et al. J. Mol. Biol. 215:403410, 1990) is available from several sources, including the National Center for Biotechnology Information (NCBI, Bethesda, Md.) and on the Internet, for use in connection with the sequence analysis programs blastp, blastn, blastx, tblastn and tblastx. A description of how to determine sequence identity using this program is available at the NCBI web site.

Sequence identity can, for example, be counted over full-length alignment with the amino acid sequence using the NCBI Blast 2.0, gapped blastp set to default parameters. For comparisons of amino acid sequences of greater than about 30 amino acids, the Blast 2 sequences function may be employed, for example, using the default BLOSUM62 matrix set to default parameters, (gap existence cost of 11, and a per residue gap cost of 1). When aligning short peptides (fewer than around 30 amino acids), the alignment may be performed using, for example, the Blast 2 sequences function, employing the PAM30 matrix set to default parameters (open gap 9, extension gap 1 penalties). Proteins with even greater similarity to a reference sequence will show increasing percentage identities when assessed by this method, such as at least 70%, at least 75%, at least 80%, at least 90%, at least 95%, at least 98%, or at least 99% sequence identity. When less than the entire sequence is being compared for sequence identity, there may be in some examples be at least 75% sequence identity over short windows of 10–20 amino acids, for example sequence identities of at least 85% or at least 90% or 95% depending on the similarity to the reference sequence.

The invention described and the disclosure made herein are susceptible of many modifications and variations, as will be apparent to, and readily performable by, the skilled reader in the light of this disclosure; and the disclosure extends to adaptations, combinations and subcombinations of the features as mentioned and/or described in the present description including the attached claims. All documents cited herein are hereby incorporated by reference in their entirety for all purposes.

What is claimed is:

1. A method of blocking binding of a chemokine capable of binding an M3 protein of MHV68 to a receptor for the chemokine on the surface of a cell, comprising
contacting the cell with a M3 protein of MHV68 which binds to the chemokine, thereby blocking the binding of the chemokine to the receptor,
wherein the chemokine, the receptor, the M3 protein of MHV68, or a combination thereof are labeled or unlabeled.

2. The method of claim 1, wherein the chemokine is a CXC, CC, C, or a CX3C chemokine.

3. The method of claim 2, wherein the chemokine is a human or a mouse chemokine.

4. The method of claim 1, wherein the chemokine is lymphotactin, RANTES, MIP-1 alpha, MCP-1, MCP-4, IL-8, murine KC, murine MIP2, human GCP2, human IP10, fractalkine, murine LIX, MIP-1, or secondary lymphoid tissue chemokine SLC.

5. The method of claim 1, wherein the cell is in vitro.

6. The method of claim 1, wherein the cell is in vivo.

7. The method of claim 1, wherein the M3 protein of MHV68 is labeled.

8. The method of claim 1, wherein the chemokine is labeled.

9. The method of claim 1, wherein the receptor for the chemokine is labeled.

10. The method of claim 1, wherein the cell is a skin cell.

11. The method of claim 1, wherein the chemokine comprises lymphotactin.

12. The method of claim 1, wherein the chemokine comprises RANTES.

13. The method of claim 1, wherein the chemokine comprises MIP-1-alpha.

14. The method of claim 1, wherein the chemokine comprises MCP-1.

15. The method of claim 1, wherein the chemokine comprises MCP-4.

16. The method of claim 1, wherein the chemokine comprises IL-8.

17. The method of claim 1, wherein the chemokine comprises human GCP2.

18. The method of claim 1, wherein the chemokine comprises human IP10.

19. The method of claim 1, wherein the chemokine comprises fractalkine.

20. The method of claim 1, wherein the chemokine comprises secondary lymphoid tissue chemokine SLC.

21. The method of claim 1, wherein the chemokine is a human chemokine.

22. A method of blocking binding of a chemokine capable of binding an M3 protein of MHV68 to a receptor for the chemokine on the surface of a cell, comprising
contacting the cell with a M3 protein of MHV68 which binds to the chemokine, thereby blocking the binding of the chemokine to the receptor
wherein the chemokine, the receptor, the M3 protein of MHV68, or a combination thereof, are labeled or unlabeled wherein the M3 protein of MHV68 is a coupled protein.

* * * * *

SEQUENCE LISTING

<160> NUMBER OF SEQ ID NOS: 2

<210> SEQ ID NO 1
<211> LENGTH: 30
<212> TYPE: DNA
<213> ORGANISM: Artificial Sequence
<220> FEATURE:
<223> OTHER INFORMATION: Primer

<400> SEQUENCE: 1
cgcgaattca tggccttcct atccacatcg        30

<210> SEQ ID NO 2
<211> LENGTH: 33
<212> TYPE: DNA
<213> ORGANISM: Artificial Sequence
<220> FEATURE:
<223> OTHER INFORMATION: Primer

<400> SEQUENCE: 2
ggtgcggccg catgatcccc aaaatactcc agc        33